United States Patent [19]

Cruz, Jr., Mamerto M.

[11] Patent Number: 4,543,410

[45] Date of Patent: Sep. 24, 1985

[54] ABSORBENT CELLULOSIC BASE STRUCTURES

[75] Inventor: Cruz, Jr., Mamerto M., Pennington, N.J.

[73] Assignee: Morca, Inc., Pennington, N.J.

[21] Appl. No.: 390,179

[22] Filed: Jun. 21, 1982

[51] Int. Cl.$^4$ .................. A61F 13/16; B32B 27/42
[52] U.S. Cl. ...................... 536/84; 604/374; 428/297; 536/63; 536/66; 536/80; 536/88; 106/196; 106/197.1; 106/197.2
[58] Field of Search ............ 604/374, 375, 376, 364, 604/368; 536/84, 63, 66, 80, 88, 56; 428/297; 106/197 R, 197 C, 196, 122

[56] References Cited

U.S. PATENT DOCUMENTS

| | | |
|---|---|---|
| 2,423,707 | 7/1947 | Kenyon et al. .............. 536/56 X |
| 2,517,772 | 8/1950 | Doub et al. ................. 536/56 X |
| 2,537,978 | 1/1951 | Eberl ........................... 536/56 X |
| 2,758,112 | 8/1956 | Waning ........................... 536/56 |
| 3,034,922 | 5/1962 | Boi ............................... 604/364 X |
| 3,055,369 | 9/1962 | Graham, Jr. ................. 604/376 X |
| 3,371,666 | 3/1968 | Lewing ......................... 604/376 X |
| 3,563,241 | 2/1971 | Evans et al. ................. 604/376 X |
| 3,589,364 | 6/1971 | Dean et al. .................. 604/376 X |
| 3,666,750 | 5/1972 | Briskin et al. ............... 128/325 X |
| 3,935,099 | 1/1976 | Weaver et al. .............. 604/368 X |
| 4,056,400 | 11/1977 | Diamantoglou et al. ... 536/56 X |
| 4,107,426 | 8/1978 | Gordon .......................... 536/56 |
| 4,248,595 | 2/1981 | Lask et al. ................... 536/84 X |
| 4,256,877 | 3/1981 | Karlsson et al. ............ 604/376 X |

FOREIGN PATENT DOCUMENTS 0737405  6/1980  U.S.S.R. ........................ 128/325

Primary Examiner—George F. Lesmes
Assistant Examiner—Nancy A. B. Swisher
Attorney, Agent, or Firm—George F. Mueller

[57] ABSTRACT

Absorbent, coherent, flexible structures in the form of fibrous webs and porous sponges comprising water-insoluble, ring oxidized cellulosic bases consisting of water-insoluble cellulose ethers, cellulose mixed ethers ring oxidized forms of these cellulose, cellulose ether mixed esters and mixtures of the bases. The cellulose bases have a DS of between about 0.05 and about 0.35. Upon application of the structures to the body and wet with aqueous body liquids, sharp edges and protruding fibers and fibrils or hairs become highly swollen or may dissolve thereby eliminating irritation. The ring oxidized forms of the cellulose bases contain between about 2% and about 52% added carboxyl groups. The structures may have hemostatic properties and the structure may include uniformly dispersed therein chitin and/or starch derivatives or contain starch or gelatin compounds to enhance the hemostatic efficacy. The structures may include water-soluble agents which function as dry binders but when the structure is wet with aqueous body liquids, the agents dissolve and become leached from the structures.

18 Claims, No Drawings

ABSORBENT CELLULOSIC BASE STRUCTURES

This invention relates to absorbent, coherent bodies or structures based upon cellulose as a precursor raw material.

Cellulose based bodies or structures, such as, for example, regenerated cellulose sponge, cellulose gauze (cotton or regenerated cellulose fiber), structureless masses of loose cellulose (cotton and regenerated cellulose) fibers and the like have been utilized to absorb body liquids and blood for medical purposes, as in a variety of surgical procedures. Although, in general, these bodies or structures are relatively inexpensive, the principal disadvantage in their use in contact with tender or sensitive areas of the body, as in the eye, abrasions, incisions and the like, is the stiffness, harshness and scratchy nature of cellulose sponges and fibers which may result in irritation. The harshness and stiffness, in some instances, may cause a rupture in the skin or membrane allowing harmful microorganisms to enter the wound. Conventional regenerated cellulose sponge contains reinforcing fibers. When the sponge is cut to desired sizes, the cut surfaces present sharp edges where the film-like structure has been severed and, in addition, fine fiber fragments are formed along the cut surfaces. In the use of such cut sponges, as in the conventional pledgets used in eye treatment and surgery, the fine fibers protruding from the cut surfaces and the cut surfaces cause irritation and loose fiber fragments may become dislodged and serve as additional sources of irritation and where the skin or membrane is broken serve as a source of infection. Further the dislodged fiber fragments may enter the incision or wound thereby introducing into the body foreign material.

The present invention provides absorbent, coherent and flexible cellulose structures which overcome the disadvantages of the prior products without detracting from the liquid absorbency of the prior products.

The present invention further provides absorbent, coherent and flexible cellulosic structures having a higher liquid absorbency than the prior products.

The present invention also provides absorbent, coherent cellulosic structures, such as cut sponges, for example, pledgets, wherein the protruding fibers, macrofibrils or "hairs" and the sharp edges of the sponge, when the structure is applied to the body and wet with aqueous body liquids, become almost instantaneously extremely high swollen or, in some instances, dissolved thereby avoiding any possible harshness or irritation.

The present invention also further provides absorbent, coherent cellulosic structures containing water soluble impregnants which may serve as binding agents in the dry state of the structure, but when wet with body liquids dissolve and become leached from the structure, as in pledgets used in eye treatment or surgical procedures and the solution serves as a lubricant.

The present invention also contemplates structures which are not only absorbent but also possess hemostatic properties.

Further advantages will become apparent from the detailed description and examples which follow.

The present invention contemplates coherent, water-insoluble but water-swellable cellulosic base structures with or without water-soluble impregnants. The cellulosic bases are cellulose ethers, cellulose mixed ethers, cellulose ether mixed esters and ring oxidized forms of these cellulose compounds having a degree of substitution (DS) of from about 0.05 to about 0.35, preferably between about 0.1 and about 0.25. The specific DS varies within the broad range depending upon the specific derivative. For example, in the case of carboxymethyl cellulose, the Ds may vary within the broad range but preferably lies within the range of 0.1 to 0.25. In the case of derivatives such as cellulose succinate, glutarate, maleate and the like, the DS preferably is within the range of from about 0.05 to about 0.3. In the case of mixed ethers, such as, for example, hydroxypropylmethyl cellulose, the total DS preferably varies from about 0.05 to about 0.25 wherein the methyl substitution may be 0.05–0.15 and the hydroxypropyl substitution may be 0.05–0.1. In the case of a cellulose ether mixed ester such as, for example, succinylated methyl cellulose, the methyl substitution may be from 0.05 to 0.2, preferably 0.1–0.15, and the succinyl substitution may be from 0.1 to 0.2. The succinate ester is utilized so as to impart to the coherent cellulosic structures hemostatic properties. The ether substitutents are primarily utilized to impart swelling characteristics.

The coherent structures are in sponge and fibrous mat forms. The sponge forms may be prepared in accordance with the conventional method of producing cellulosic sponges by the viscose process or the conventional methods of producing such sponges from cellulose esters. Following thorough washing and purification of these types of sponges, the sponge comprising the porous cellulose structure and contained cellulose reinforcing fibers is derivatized. Alternatively, a sponge-like structure may be formed by freeze drying an aqueous-organic solvent slurry of cellulose derivative fibers. The fibrous mat structures may be formed by any desired conventional method normally used to prepare non-woven cellulose fiber mats followed by derivatizing the cellulose fibers which may be natural or regenerated cellulose. Alternatively, the cellulose fibers may first be derivatized prior to forming the non-woven mat. Preferably, the derivatized fibers are dispersed or slurried in a liquid medium comprising water and a water-miscible organic solvent such as, for example, ethanol, isopropanol, acetone and the like. The mat is formed by sheeting the fibers and freeze drying the mat, preferably pressing the sheeted fiber mat to expel excess liquid prior to freeze drying.

Derivatization of the cellulosic base may be effective in any conventional manner. Agents useful in derivatization are known and include compounds, such as, for example, ethylene oxide, propylene oxide, butylene oxide, methyl chloride, ethyl chloride, chloroacetic acid, methyl chloride and ethylene oxide, methyl chloride and propylene oxide (the combination for the preparation of ether-esters), succinic anhydride, glutaraldehyde, maleic anhydride and the like.

For the preparation of fibrous mats, any desired cellulosic fibers such as chemically purified wood pulp fibers, cotton linters, regenerated cellulose fibers and the like are satisfactory. Preferably, the raw material is highly fibrillated, chemically purified wood pulp having a CSF (Canadian Standard Freeness) not exceeding about 150, but preferably 50 or below. This type of raw material is highly fibrillated and derivatization results in a product of higher absorbency. Also the coherent fibrous mat will possess a greater proportion of protruding macrofibrils and microfibrils or "hairs" which are more readily derivatized and hence more rapidly highly swollen when wet with body liquids. Although the fibers may be first formed into the coherent mat and then derivatized, preferably the fiber raw material is derivatized prior to converting the fibers into a coherent mat. By first derivatizing the fibers a more uniformly derivatized structure is obtained. In view of the fact that in most instances derivatized fibers are more sensitive to aqueous liquids, in forming the sheeted webs or mats, the derivatized fibers are slurried in a liquid medium comprising water and a water-miscible organic solvent. The relative proportions of water and organic solvent are varied depending upon the specific DS of the derivatized cellulosic fiber. In general, the higher the DS, the greater the proportion of the organic solvent, as will be apparent from the examples. The use of the water-organic solvent media is essential so as to provide the coherent structure with the desired compactness, flexibility and absorbency. Because of the water sensitivity of the derivatized fibers, slurrying of such fibers in water alone while resulting in highly coherent mats, the mats are harsh and stiff and of low absorbency.

The following examples illustrate the preparation of derivatized cellulosic fibers of low DS, of coherent mats formed therefrom and the characteristics of the fibers and coherent mats.

EXAMPLE 1–3

In the preparation of carboxmethyl cellulose fibers, highly fibrillated, chemically purified wood pulp fibers (CSF of about 50) were utilized. 30 grams of the pulp fibers were slurried in 772 gms. of an aqueous liquid consisting of azeotropic isopropanol. In each instance various volumes of a 20% caustic soda solution were added to the slurries while the slurries were at ambient temperature. In order to obtain the stated DS of the carboxymethyl cellulose fibers, stated amounts of chloroacetic acid dissolved in 8 gms. of 100% isopropanol were added to the slurries. The mixtures were then heated to 50° to 55° C. and maintained at the elevated temperature for 5 hours while mildly agitating the slurries. The derivatized fibers were recovered by filtration and the recovered fibers washed by slurrying in azeotropic isopropanol and again recovered by filtration. The washing procedure was repeated three times. Each washing was effected by slurrying the fibers in about 300 mls. of the azeotrope. The finally recovered fibers were then slurried in about 250 mls. of 100% isopropanol. The fibers recovered from the final washing were vacuum dried at 45°–50° C. The fibers as thus prepared comprise a sodium salt of carboxymethyl cellulose. If desired, following the derivatization step, appropriate amounts of an acid such as hydrochloric acid may be added to convert the sodium salt to the free acid form.

In the preparation of air dried, coherent mats, samples of the dried fibers were slurried in both water-ethanol and water-isopropanol media to form slurries of approximately 0.1% consistency. The fibers were sheeted on a 100 mesh sieve and the major portion of the liquid media removed by suction. Another 100 mesh sieve was placed over the formed sheet and a pulp sheet blotter placed over the upper sieve and a like pulp sheet blotter placed beneath the lower sieve. A 3 pound roll was passed over the assembly to expel excess liquid. The sheet was removed and dried in a circulating air oven at 45° C.

In the preparation of freeze dried coherent mats or sheets, the same procedure was followed except the samples of the dried derivatized fibers were slurried in media containing lower proportions of the organic solvents to form slurries of about 10% consistency. Following the pressing to expel excess liquid the mats or sheets were freeze dried.

As a control, 30 grams of the wood pulp fibers were subjected to washings with azeotropic isopropanol and 100% isopropanol and vacuum dried at 45°–50° C. Samples of the dried fibers were slurried in water-ethanol and water-isopropanol media and mats formed as described for the preparation of mats from the derivatized fibers.

The physical properties of the mats as prepared are reported in Table I. The sample mat sizes, thickness values and weights as set forth in the table are averages of at least 6 samples of mats prepared as described. It will be noted that the mats prepared from slurries of the derivatized fibers in ethanol-water media and isopropanol-water media are substantially identical in the physical properties and, hence, only single values are set forth in the table.

Table II sets forth the properties exhibited by microscopic observations at a magnification of 400X when samples of the webs and of the fibers were wetted with an isotonic saline solution. Again, the observations for webs prepared from ethanol-water and isopropanal-water media and when air dried and freeze dried are substantially identical.

As shown by the data in Tables I and II, when preparing slurries for the formation of mats, in order to avoid producing a high degree of bonding between the fibers, the higher the DS of the fibers, the greater the relative proportion of the alkanol required in the slurrying liquid. Also, in order to provide sheets or mats having substantially identical physical properties dried by air drying requires a higher proportion of the alkanol than those dried by freeze drying. The data further illustrates that when mats and fibers are wetted with an aqueous liquid, the higher the DS of the fibers, the greater the degree of swelling. Although the cellulose fibers of the control mats when wetted exhibit "hairs" protruding from the fiber surfaces and ends, no such "hairs" are visible on the wetted cellulose derivative fibers. The lumen width of the wetted cellulose fibers is not altered, the reduction in the lumen width varies directly with the DS of the derivatized fibers. Similarly, the fiber width increases directly with the DS. When the wetted fiber is placed between glass plates and pressure is applied, the flattening of the fibers increases directly with the DS.

EXAMPLE 4

In the preparation of hydroxypropylmethyl cellulose fibers, the same highly fibrillated, chemically purified wood pulps fibers as used in Examples 1–3 were utilized. Methyl cellulose fibers were first prepared by slurrying 25 parts of the pulp fibers in 20 parts of a 20% solution of caustic soda and about 700 parts of azeotropic isopropanol by mixing for about 30 minutes in a closed vessel. A mixture of 4 parts of methyl chloride in about 8 parts of azeotropic isopropanol was introduced into the vessel and mixing continued for about 2.5 hours while maintaining the mixture at a temperature of 30°–35° C. Approximately 4 parts of propylene oxide in 4 parts of azeotropic isopropanol was then introduced into the vessel and the mass agitated for an additional 4.5 hours while maintaining the mass at a temperature of 35°–40° C.

The hydroxypropylmethyl cellulose fibers were recovered by filtration and washed by slurrying in azeotropic isopropanol and separated by filtration. Washing was repeated three times. Following this washing procedure, the fibers were subjected to a final wash with 100% isopropanol. Where the product is intended for use in surgical procedures, the isopropanol in the reaction mixture is replaced with ethanol, the first four washing steps utilizing 200 proof (100%) ethanol. The ethanol substitution is utilized because it is difficult to remove traces of isopropanol. Following washing, the fibers may be dried in an air circulating oven at about 50° C., but preferably vacuum dried at 45°–50° C. The derivatized fibers thus prepared had a methyl substitution equivalent to a DS of 0.1–0.15 and a hydroxypropyl substitution equivalent to a DS of 0.05–0.1. The total substitution is equivalent to a DS of about 0.15 to about 0.26. In order to insure removal of all sodium hydroxide an appropriate amount of an acid such as hydrochloric acid may be added to the fibers recovered from the reaction mass prior to washing. It is obvious that by varying the amounts of methyl chloride and propylene oxide, the relative degrees of methyl and hydroxypropyl substitution may be varied as desired. In all instances, however, the total substitution should not exceed a total DS of about 0.3.

Coherent mats and sheets may be formed in the same manner as described in Examples 1–3. Alternatively, followng final washing, the derivatized fibers need not be dried but may be slurried directly in aqueous isopropanol or aqueous ethanol to form dilute slurries as described in Examples 1–3. Coherent mats formed from slurries in the two media are substantially identical in properties. The microscopic observations at a magnification of 400X when the mats are wet with a 0.9% saline solution are substantially identical to those observed for Example 2.

EXAMPLE 5

In the preparation of succinylated carboxymethyl cellulose, carboxymethyl cellulose of a DS of 0.1–0.13 was prepared as described in Example 1. A mixture of 4 parts of succinic anhydride, 10 parts of sodium acetate and 80 parts of glacial acetic acid was prepared. To this mixture, 30 parts of the carboxymethyl cellulose fibers were added and the mass agitated for about 3 hours at 35°–40° C. The succinylated carboxymethyl cellulose fibers were recovered by filtration and the fibers washed with ethanol or isopropanol as described in Example 4. The fibers had a succinyl substitution equivalent to a DS of 0.1–0.2. Similar succinylated carboxymethyl cellulose fibers were also prepared by the use of carboxymethyl cellulose fibers as described in Examples 2 and 3. Obviously, succinylated carboxymethyl cellulose fibers having succinyl substitution of higher DS may be prepared by increasing the relative amounts of succinic anhydride. In all instances, however, the total substitution should not exceed about a DS of about 0.35.

Coherent mats may be prepared as described in Examples 1–4. Mats formed from slurries in aqueous ethanol and aqueous isopropanol are substantially identical in properties. Microscopic observations of the succinylated carboxymethyl cellulose fibers as prepared above are substantially identical to those of Example 2.

Conventional regenerated cellulose sponge is formed from a mixture of viscose, reinforcing fibers, for example, regenerated cellulose fibers, cotton, linen and the like and a pore forming salt high in water of crystallization. This class of salt includes sodium sulfate decahydrate, sodium carbonate decahydrate, trisodium phosphate decahydrate, sodium acetate trihydrate, potassium sodium tartrate tetrahydrate and the like. The viscose may contain from 5 to 8% cellulose, 6 to 100% fibers, based on the cellulose, and 900 to 2500% of the pore forming salt, based on the cellulose. The pore size in the sponge is directly related to the size of the pore forming salt crystals. As is conventional, the viscose mixture is cast in a desired mold, the cellulose solution coagulated, usually by heat, and the cellulose then regenerated. The shaped mass is then washed thoroughly to remove soluble salts, desulphurized and bleached.

EXAMPLE 6

Sponge was prepared from viscose containing 6% cellulose, 7% caustic soda, 30% carbon bisulfide, based on cellulose, 25% of the highly fibrillated chemically purified wood pulp fibers and 1500% sodium sulfate decahydrate. The preparation of derivatized sponge structures followed the procedure utilized in forming the derivatized fibers. In the preparation of carboxymethyl cellulose sponge (regenerated cellulose and cellulose reinforcing fibers), four 1.8 gm. samples of sponge, each about 6 cm.×6 cm.×0.7 cm., were submerged in 400 ml. of azeotropic isopropanol. In each instance various volumes of a 20% caustic soda solution were added and the sponges agitated in the liquid for about ¾ hour. Various amounts of chloroacetic acid in 8 gms. of isopropanol were added and the sponges agitated in the liquid for 2½ to 5 hours while maintaining the temperature at 50°–55° C.

The derivatized sponges were removed from the liquid, the liquid allowed to drain and the excess liquid then expressed from the sponges. The sponges were then treated with dilute isopropanol solutions containing a drop or two of concentrated hydrochloric acid to neutralize the remaining absorbed caustic soda. The sponges were then subjected to a washing treatment by squeezing them several times while immersed in azeotropic isopropanol, removing and pressing them to expel excess liquid and repeating the procedure 3 additional times, each time using fresh azeotropic isopropanol to remove the reaction liquor and salt. Following the fourth washing, the sponges were washed with 100% isopropanol and after pressing out excess isopropanol, the sponges were dried in an air circulating oven at about 45° C. As a control, three 1.8 gm. samples of spongeware subjected to washings with azcotropic isopropanol and 100% isopropanol and dried in an air circulating oven at about 45° C. Properties of the sponges are shown in Table III.

It will be noted that in the formation of derivatized sponges of about the same DS values as those of the fibers, lesser amounts of chloroacetic acid were used. The regenerated cellulose has a degree of polymerization of about one-quarter that of the wood pulp fibers and, hence, the smaller the amounts of the acid to form derivatives of about the same DS.

As shown by the data, the reaction of the sponge structures to saline solution follows the reaction of the fibers to such aqueous liquid. It is pertinent to note that when the sponges are wetted with the aqueous liquid, the "hairs" at cut suraces disappear and the sharp cut edges become swollen and blunted, the higher the DS the greater the degree of swelling. At the upper DS, the sponge becomes so highly swollen it approaches a gel state.

Derivatized cellulose sponges having higher liquid absorbencies may be prepared by mixing with the viscose, preferably prior to the addition of the fibers and pore forming salt, an alkali-soluble polyacrylate or polymethacrylate or copolymer of acrylic and methacrylic acids. The amount of acrylic additive may vary from about 1 to 15%, preferably 7 to 10%, based on the cellulose. An example of a satisfactory additive of this class is the Rohm and Haas Co., commercially available Acrysol ASE-108, a 20% solution having a Brookfield LVF viscosity at 25° C. (#1 spindle, 12 rpm.) of 200 cps. The mixture of the addition of the fibers and pore forming salt is then cast, the cellulose solution coagulated, the cellulose regenerated and treated as above described.

As an alternative, starch, particularly amylose starch, such as, for example, National Starch and Chemical Corporation Hylon VII (70% amylose content), may be used as an additive. Following regeneration of the cellulose to form the cellulose-starch sponge structure, the sponge may be derivatized as described above. An effective hemostatic product may be obtained by first preparing a methyl derivative followed by forming a succinyl derivative of the cellulose and amylose.

As an alternative for the production of products having highly efficaceous hemostatic properties, chitin (a poly-$\beta$-(1→4)-N-acetyl-D-glucosamine), a polyhydroxyl biopolymer similar to cellulose, may be added to the viscose prior to the addition of the reinforcing fibers and pore-forming salt. The amount of chitin added may vary up to about 30%, preferably 7 to 15%, based on the cellulose. The sponge is prepared in the conventional manner. In forming a derivative, for example, the cellulose and chitin both become derivatized, as in preparing a succinyl derivative which is a highly effective hemostat.

In producing derivatized products, either fibrous or sponge structures, the base material may be converted first into a methyl derivative of the desired DS. The methyl derivative is then converted into a hydroxypropylmethyl derivative or into a succinylated methyl derivative or succinylated hydroxypropylmethyl derivative of desired DS. It is obvious that the specific derivatized cellulose structure may be prepared with specific substituents based upon the intended use for the structure and the desired properties of the structure.

Coherent structures, both fibrous mat and sponge forms may be impregnated with azeotropic isopropanol or ethanol solutions containing gel-free, water-soluble and aqueous isopropanol or aqueous ethanol soluble hydroxypropylmethyl cellulose and methyl cellulose. Such hydroxypropylmethyl cellulose compounds have a hydroxypropyl DS of about 0.11–0.30 and a methyl DS of about 1.5–2.2. The methyl cellulose derivatives have a DS of about 1.5–2.2. The impregnating solutions may contain from about 0.02 to about 0.50% of the desired impregnant. Following impregnation, the cellulose derivative impregnant may be precipitated within the structure by immersion of the impregnated structure in 100% isopropanol, or 100% ethanol. After draining, the impregnated structures are vacuum dried at about 45° C.

If desired, the vacuum dried structures may be compacted without decreasing the absorbency of the structures. The vacuum dried structures are conditioned to contain between about 7 and 15% moisture which may be effected by maintaining the structures in ambient atmosphere at about 23° C. and a RH of about 50% for 24 hours. The fibrous mat structures may be pressed to reduce the thickness to 40 to 60% of the original thickness of the conditioned mats. In the case of sponge structures, they may be reduced by as much as 90% of the original thickness.

In the dried or dried and compacted structures, the impregnants function as dry binders. Upon wetting these structures with aqueous liquids, such as body liquids, the water soluble derivatives dissolve and are released. For example, pledgets when used in eye treatments and dabbed on the eye, absorb rapidly the liquid, swell, the derivative dissolves and is released into the tear. The released derivative serves as a lubricant and cushioning agent. Depending upon the DS of the cellulose base structure, the macrofibrils and microfibrils become highly swollen and may also dissolve, thus there may be a dual source of water-soluble material to function as a soothing lubricant. Other water-soluble dry binders satisfactory include hydroxypropylmethyl cellulose, carrageenin, alginates, dextran and the like may be used in lieu of the above used agents.

If desired the structures also may be impregnated with aqueous isopropanol or ethanol solutions of germicides, moldicides, bacteriocides, pharmaceuticals and the like, such as, for example, bacitrin, proccine, methiolate, ephedrine, cortisone, iodine and carbacol. Obviously, upon drying the structures, these agents remain within the structure. Upon wetting as with an aqueous body liquid, the agent dissolves and is slowly released.

EXAMPLE 7

Coherent structures, both fibrous mat and sponge forms, were impregnated with azeotropic ethanol solutions containing gel-free, aqueous ethanol soluble hydroxypropylmethyl cellulose (hydroxypropyl DS 0.2, methyl DS 1.9) and methyl cellulose (DS 2.3). The fibrous mats were as prepared in accordance with Example 2 and the sponge form, prepared as in Example 6. The impregnating solutions contained about 0.7% of the cellulose derivative. Samples of the fibrous mats were submerged in the impregnating solutions, withdrawn and again immersed in order to insure a complete impregnation of the mats. In the case of the sponge samples, these were immersed in the impregnating solutions and squeezed three times while immersed to insure a complete impregnation. Following the impregnating procedure, the samples were withdrawn and excess liquid allowed to drain. The structures were then immersed in 100% ethanol to precipitate the respective cellulose derivatives in the structures.

After withdrawing the respective structures excess liquid was drained and the structures vacuum dried at about 50° C. to remove the remaining liquid. The vacuum dried samples were allowed to remain in the laboratory ambient atmosphere, 22° C., 50% RH, for about 20 hours. The mat samples had about 10% moisture while the sponge samples had about 12% moisture. The mat samples were compacted from an original thickness of 3 mm. to a finished thickness of 1.5 mm. The sponge samples were compacted from an initial thickness of 0.7 cm. to a finished thickness of about 0.4 cm. The liquid absorbencies of the impregnated and compressed mats and sponges were substantially identical to the liquid absorbencies of the pre-compressed structures.

In general, the fibrous mats of derivatized cellulose fibers exhibit a higher percent water absorption than the sponge forms. This is attributed by the freeness of the fibers to swell when wet with aqueous liquids. In the sponge structures, the structure consists of interconnected film-like units which define pores and, hence, while the fibers in the mat form can swell in all transverse directions, the film-like units can swell in directions only normal to the film surface. Assuming a mat and sponge both of the same weight and approximately the same DS, the mat will exhibit a higher liquid absorbency than the sponge. This is illustrated by the data in Table IV. As will be noted from the Table, the structures absorb at least 1000%, by weight based upon the dry weight, of water or aqueous liquids.

In determining the percent absorption of liquids, the dry sample is weighed, the sample then immersed in the liquid, the sample after complete wetting is removed and excess liquid drained without pressing. The wet sample is then weighed and the percent absorption calculated from the weight determinations. It will be noted from the Table IV that as the DS increases, the percent absorption increases. It will be further noted that as the DS approaches the upper limit of DS 0.35, the percent absorption decreases. This occurs because at the upper DS a portion of the sample is so highly swollen that it is almost in a gel state and such portion drains with the excess absorbed liquid. The values in Table IV are averages of duplicate sample determinations.

It is apparent that in the sponge structures including the polyacrylates, chitin derivatives and/or starch derivatives, these additive substances will be intimately and uniformly distributed throughout the sponge along with the cellulose derivative.

The foregoing relates to cellulose derivatives; that is, where the derivatives are cellulose ethers, cellulose mixed ethers, cellulose ether mixed esters and these compounds mixed with other polymers such as chitin, starch and polyacrylates, and are referred to herein collectively and in the claims as the cellulosic bases.

In order to further improve the structures for surgical purposes and increase the hemostatic efficacy with or without imparting bioassimilability or bioabsorbability characteristics, but maintaining the advantages as discussed above, some of the anhydroglucose units of the cellulosic bases are subjected to ring oxidation. Ring oxidation converts selectively the hydroxyl groups at the 2, 3 and 6 positions of the anhydroglucose unit into carboxyl groups, depending upon the specific oxidant. Dinitrogen tetroxide converts the hydroxyl group at the 6 position into a carboxyl group to produce a monocarboxyl form of the base. Periodic acid will open the ring between the 2 and 3 positions and convert the hydroxyl groups at the 2 and 3 positions into aldehyde groups. The dialdehyde is subjected to chlorus acid whereby the aldehyde groups are converted into carboxyl groups to produce a dicarboxyl form of the base. The hydroxyl group at the 6 position of the dicarboxyl form may be oxidized with dinitrogen tetroxide to produce a tricarboxyl form of the base. Alternatively, the dialdehyde form may be converted directly into the tricarboxyl form by treatment of the dialdehyde with dinitrogen textroxide.

The number of anhydroglucose units in the cellulosic base base wherein the hydroxyl groups at the 6 position are converted to a carboxyl group is dependent upon the ratio of the amount of cellulosic base to the amount of dinitrogen tetroxide, the temperature and the time of the reaction. The number of anhydroglucose units wherein chain scission occurs between the 2 and 3 position will be dependent upon the concentration of the periodic acid, pH, time and temperature. Upon scission, there is formed aldehyde groups at the 2 and 3 positions. The aldegyde groups are then converted to carboxyl groups by treatment with small excess amounts of chlorus acid.

The conversion of all of the hydroxyl groups at the 6 position of all of the anhydroglucose units of the cellulose corresponds to a maximum calculated carboxyl content of 25.6%. The conversion of all of the hydroxyl groups at the 2 and 3 positions of all of the anhydroglucose units of the cellulose corresponds to a maximum calculated carboxyl content of 46.9%. The conversion of all of the hydroxyl groups at the 2,3 and 6 positions of all of the anhydroglucose units of the cellulose corresponds to a maximum calculated carboxyl content of 65.53%.

The following example illustrates the preparation of ring oxidized carboxymethyl cellulose sponges and control ring oxidized cellulose sponges wherein oxidation is effected at the 6 position:

EXAMPLE 8

Samples of regenerated cellulose sponge were cut to a size of $3 \times 3 \times 0.25$ in. ($7.62 \times 7.62 \times 0.635$ cm.), each weighing about 2.63 gms. The samples were divided into 8 groups. The samples of two groups were used as controls. The samples of the remaining groups were converted into carboxymethyl cellulose of varying DS as described in Example 6 and analyzed for their carboxyl group contents. A mixture was prepared containing 10 parts by weight dinitrogen tetroxide and 90 mls. methylene chloride. One group of control samples and three groups of sponges etherified to 3 different DS's were immersed in batches of dinitrogen tetroxide-methylene chloride mixtures at room temperature and the mass agitated mildly for about 25 hours. In each instance about 1 part by weight of sample was used to about 2 parts by weight dinitrogen tetroxide. The other group of control samples and the other three groups of etherified sponges were immersed in like batches of dinitrogen tetroxide in the same ratios of sample to dinitrogen tetroxide at room temperature and agitated for about 55 hours. In both reactions, the amount of dinitrogen tetroxide was used in excess amounts for the reaction. Following the reaction periods, the samples were washed free of the reaction liquid with azeotropic isopropanol, dried and analyzed for the carboxyl content due to ring oxidation. The carboxyl contents due to the carboxymethyl group and due to the ring oxidation are reported in Table V.

Alternatively, the ring oxidation of the cellulosic base may be effected in a dry system. For example, in a 1 liter reactor, 30 gms. of regenerated cellulose sponge may be treated with about 50 gms. of nitrogen tetroxide at room temperature. By conducting the reaction for about 30 hours, the carboxyl content will be between about 12 and 15%. By conducting the reaction for about 60 hours, the carboxyl content is about 21%. As a further alternative, the cellulosic base may be exposed to dinitrogen tetroxide gas at room temperature followed by further oxidation in a methylene chloride dinitrogen tetroxide mixture at room temperature to provide the desired ring oxidation.

As stated above the DS of the cellulosic base should not exceed about 0.35. The proportion of carboxyl content in the monocarboxyl form of the cellulosic base may vary from about 2 to about 21%. Where the DS of the derivatized cellulosic base is 0.35, upon wetting the base (fibrous or sponge) the base becomes gelatinous and loses its physical structure. Significant characteristics of products, particularly cellulosic bases having a DS of 0.35 subjected to ring oxidation and having the added carboxyl content are a reduced swelling and the ability to retain the physical structure when wetted with aqueous liquids without becoming gelatinous.

Ring oxidized cellulosic base sponges having a carboxyl content due to ring oxidation up to about 15% may be considered as of medium carboxyl content and may be classed as surgical hemostats. Where the carboxyl content due to ring oxidation exceeds about 15%, the product may be considered as of high carboxyl content and in addition to its classification as a surgical hemostat is bioabsorbable or bioassimilable.

Ring oxidation is applicable to the cellulosic bases in any derived physical form as well as to starch, particularly high amylose starch, for the production of hemostatic agents. In the following example cellulose in several physical forms and a high amylose starch (Hylon VII-70% amylose content National Starch and Chemical Corporation) were subjected to ring oxidation to form dicarboxyl forms of the bases.

EXAMPLE 9

Cellulose powder (non-fibrous, microcrystalline cellulose), highly fibrillated, chemically purified wood pulp fibers (CSF of about 50) as used in Examples 1-3, cotton surgical gauze, regenerated cellulose sponge as described in Example 6 and Hylon VII amylose starch were used as raw materials. For each of the raw materials, solutions were prepared by dissolving 16 gms. of sodium periodate in 400 ml. deionized water heated to 45°–50° C. After cooling to room temperature the pH was adjusted to 4-5 by the addition of glacial acetic acid. In each instance 8-10 gms. of the raw material was added to the periodate solution and the solution was agitated by means of a magnetic stirrer for about 10 hours.

After the reaction period the solids were separated from the solution and the solids washed with slightly acid water containing a small amount of sodium sulfite to remove unreacted periodic acid. The wet solids separated from the wash solution were then washed with deionized water to remove any free sulfurous acid. The separated solids consisting of dialdehyde products were then treated with a solution of 150 ml. deionized water containing 10 gms sodium chlorite, the solution being adjusted to a pH of 3-4 with glacial acetic acid for 3-4 hours at room temperature. The solids were then separated from the solution, washed with deionized water containing a small amount of sodium sulfite to remove unreacted chlorus acid and subsequently washed with deionized water to remove any salts. The dicarboxyl forms of the bases were then washed with azeotropic isopropanol and vacuum dried at 45° C. The carboxyl content of the dicarboxyl forms of the bases is reported in Table VI.

Portions of the dicarboxyl forms of the bases were converted to tricarboxyl forms by ring oxidation with dinitrogen tetroxide. For each of the products, solutions were prepared containing 10 gms. by weight dinitrogen tetroxide in 90 mls. methylene chloride. The dicarboxyl forms were treated with appropriate amounts of the solution for 55 hours at room temperature as described in Example 8. The carboxyl content of tricarboxyl forms the bases is set forth in Table VI.

As an alternative procedure, the tricarboxyl forms of the bases may be prepared by the ring oxidation with dinitrogen tetroxide of the dialdehyde forms of the bases.

The dicarboxyl and tricarboxyl cellulose products in the form of sponges have hemostatic properties. However, this form of cellulose sponge has the disadvantages of the unreacted regenerated cellulose sponge as discussed hereinbefore, in spite of their appreciable carboxyl contents. In order to overcome these inherent disadvantages, it is necessary to form derivatives such as described with respect to regenerated cellulose sponge. The following example illustrates the formation of an etherified dicarboxyl and tricarboxyl form of sponge.

EXAMPLE 10

The dicarboxyl and tricarboxyl forms of sponge as prepared in Example 9 were etherified with chloroacetic acid as described in Example 2 to form carboxymethyl derivatives of the dicarboxyl and tricarboxyl forms having a carboxymethyl DS of about 0.25. The carboxyl content of the dicarboxyl and the tricarboxyl sponges and the total carboxyl content of the etherified sponges are set forth in Table VII.

As described above, the cellulosic structures may be impregnated with certain water-soluble substances which function as dry binding agents, but when the structures are wetted with body liquids, the agents dissolve and serve additional purposes. The structures may be impregnated with other substances which may function as dry binding agents, but when the structures are wetted with body liquids serve to impact hemostatic properties to the cellulosic base.

EXAMPLE 11

Fibrous webs of carboxymethyl cellulose fibers were prepared as described in Example 2. Dicarboxyl and tricarboxyl forms of starch (Hylon VIII amylose starch) were prepared as described in Example 9. Dispersions of the ring oxidized starch compounds were prepared in caustic soda solutions having a pH of 10-12, the dispersions containing approximately 2% by weight of the respective starch compounds. Carboxymethyl cellulose fiber webs were soaked in the respective dispersions for about 5 minutes. Upon removing the mats from the liquid, excess liquid was allowed to drain, the mats placed on a fine mesh screen and suction applied lightly to remove additional liquid. Azeotropic isopropanol containing a small amount of hydrochloric acid was then poured over the mats to precipitate the starch compounds in the mats. The mats were washed free of acid with azeotropic ethanol. Some of such mats were vacuum dried at about 50° C. The remaining mats wet with azeotropic ethanol were placed in a mixture of 40% ethanol and 60% water, by volume, and the mass agitated so as to disintegrate the mats and form a fiber slurry containing about 5% fibers, by weight. The slurry was placed in a tray and the slurry freeze dried. The dried products contained an average of about 1% added starch compounds. The added starch compound may vary, preferably not above about 10%. The physical structure of the vacuum dried mats resembled the physical structure of the mats of Examples 1-3. The freeze dried mats were about 1 cm. in thickness and of a fibrous sponge-like structure.

EXAMPLE 12

Carboxymethyl cellulose sponges having a DS of about 0.23 were prepared as described in Example 6.

Succinylated gelatin was prepared by dispersing or dissolving 22 gms. of food grade gelatin (pork skin type) in 200 mls. of deionized water at about 45° C. The pH was adjusted to pH 10 by the addition of dilute caustic soda (20%) solution. Approximately 2 gms. of powdered succinic anhydride was added to the solution with vigorous mixing at 45°-50° C. for 20 minutes. After the reaction, the pH of the solution was 5-5.5. The acylated mixture was deionized by the use of ion exchange resin and the solution then evaporated to dryness. Recovered succinylated gelatin was dissolved in water to form a 2% solution. The sponge samples were immersed in the solution, squeezed several times, withdrawn and allowed to drain. Some samples were squeezed lightly to express excess liquid and vacuum dried at about 50° C. Other samples without squeezing to remove excess liquid were freeze dried. The samples had a pick-up of about 1.5%. In the case of the freeze dried samples, the succinylated gelatin formed foam-like coatings within the pores and on the surface whereas the vacuum dried samples had film-like coatings.

The products of Examples 11 and 12 because of the specific coatings, in addition to the properties described above have hemostatic properties as compared to the web and sponges of Examples 2 and 6, respectively. As is obvious, the amount of the added substances may be increased by increasing the concentration of the impregnants in the impregnating solution. Although the specific impregnants are illustrated as being added to carboxymethyl cellulose fiber mats and sponge structures, they may be used as impregnants for the other cellulosic bases and ring oxidized cellulosic base structures.

In order to clarify the discussion and claims, the term "DS" is used to designate the degree of substitution of the cellulosic bases, that is, the number of ether, mixed ether or ether mixed ester groups per anhydroglucose unit. The "percent added carboxyl" is used to designate the carboxyl content by weight, added to the cellulosic base by ring oxidation.

In summary, the improved absorbent structures, fibrous and sponge forms, comprise cellulosic bases and ring oxidized cellulosic bases with or without impregnants. The cellulosic bases include, for example, cellulose ethers, mixed ethers and ether mixed esters and these substances mixed with other polymers such as chitin, starch and polyacrylates. The cellulosic bases have a DS of between about 0.05 and about 0.35. The ring oxidized cellulosic bases contain from about 2% to about 52%, by weight, added carboxyl content depending upon the extent of ring oxidation considering the positions at which oxidation has occurred. The ring oxidized forms of the substances have a carboxyl content of from about 2% to about 21%, preferably 5 to 18%, in the monocarboxyl form. In the dicarboxyl form the substances have a carboxyl content of from about 7% to about 38%, preferably 9 to 30%. In the tricarboxyl form the substances have a carboxyl content of from about 12% to about 52%, preferably 23 to 39%. The impregnants include a wide variety of substances such as, for example, germicides, moldicides, bacteriocides, pharmaceuticals and the like which are released when the structure is wetted with body liquids. Other impregnants may serve as dry binding agents or coatings in the dry state of the structures but when wetted with body liquids are released to serve other purposes such as a soothing lubricant.

TABLE I

| | Example | | | |
|---|---|---|---|---|
| | control | 1 | 2 | 3 |
| Degree of substitution | 0 | 0.11 | 0.24 | 0.33 |
| Pulp, gms. | 30 | 30 | 30 | 30 |
| Azeotropic IPA, gms. | — | 722 | 722 | 722 |
| 20% NaOH soln., gms. | — | 20 | 40 | 60 |
| ClCH$_2$COOH, gms. | — | 2 | 4 | 6 |
| 100% IPA, gms. | — | 8 | 8 | 8 |
| Air dried fiber mats from 0.1% slurries in | | | | |
| Ethanol/water, V/V | 40/66 | 55/45 | 67/33 | 75/25 |
| IPA/water, V/V | 25/75 | 37/63 | 57/43 | 70/30 |
| Freeze dried fiber mats from 10% slurries in | | | | |
| Ethanol/water, V/V | 25/75 | 35/65 | 50/50 | 65/35 |
| IPA/water, V/V | 15/85 | 25/75 | 40/60 | 55/45 |
| All mats coherent, flexible and soft to touch | | | | |
| Size, sq. cm. (Av.) | 36 | 36 | 36 | 36 |
| Thickness, mm. (Av.) | 4.0 | 3.1 | 3.0 | 3.1 |
| Weight, gms. (Av.) | 1.20 | 1.22 | 1.21 | 1.23 |

TABLE IV

Liquid Absorption

| Fibrous Mat Form | | | | |
|---|---|---|---|---|
| Degree of Substitution | Control | 0.11 | 0.24 | 0.33 |
| % Absorption | 1790 | 2410 | 3200 | 1957 |
| Sponge Form | | | | |
| Degree of Substitution | Control | 0.11 | 0.23 | 0.35 |
| % Absorption | 990 | 1090 | 1338 | 939 |

TABLE II

Microscopic observation (400X), Wet with 0.9% saline solution

| | | Example | | |
|---|---|---|---|---|
| | Control | 1 | 2 | 3 |
| Fibers | | | | |
| Lumen width | Retained | Reduced by 20% due to hydration | Reduced by 50% due to swelling | Reduced 80-90% due to swelling |
| Fiber width | Slight increase | Increased 5-10% | Increased 15-35% | Increased over 50% some disintegration |
| Pressure-fiber between glass slides | No effect | Small amt of flattening | Flattened | Almost gel-like |
| Mats | | | | |
| Fiber structure | Retained | Retained-slight hydration | Swollen | Highly swollen |
| Fiber ends | Presence of hairs | No hairs visible | No hairs visible | No hairs visible |

TABLE VII

| Base | % COOH | Total % COOH Etherified sponge |
|---|---|---|
| Dicarboxyl sponge | 8.55 | 13.55 |
| Tricarboxyl sponge | 24.95 | 30.15 |

TABLE III

| | Samples | | | |
|---|---|---|---|---|
| | Control | 1 | 2 | 3 |
| Degree of substitution | 0 | 0.10 | 0.23 | 0.35 |
| Sponge, wt. gms. | 5.4 | 7.2 | 7.2 | 7.2 |
| Azeotropic IPA, gms. | — | 400 | 400 | 400 |
| 20% NaOH soln., gms. | — | 8 | 13 | 17 |
| ClCH$_2$COOH, gms. | — | 1.2 | 1.6 | 3.0 |
| 100% IPA, gms. | — | 8 | 8 | 8 |
| Microscopic observation (400X), Wet with 0.9% saline solution | | | | |
| Cut edges | Hairs and sharp cut | No hairs, blunted | No hairs, swollen | No hairs, edges |

TABLE III-continued

| | Samples | | | |
|---|---|---|---|---|
| | Control | 1 | 2 | 3 |
| | edges | cut edges | edges | highly swollen, partially gelatinized |
| Pore structure | Rigid pores | Rigid pores size as in control | Swollen, coherent, pores smaller | Swollen, almost complete breakdown of pores |
| Physical structure, wet state | Coherent, resilient, retains structure | Coherent, resilient, retains structure | Coherent, loses resiliency upon compressing | Breakdown of structure into gel. |
| Dried from wet state | Coherent, resilient, retains structure | Coherent, resilient, retains structure | Coherent, partial loss of structure | Complete loss of structure |

TABLE V

| Group | DS | % COOH | % COOH (1) |
|---|---|---|---|
| 1 | 0 | 0 | 8.5 |
| 2 | 0.10 | 2.05 | 9.1 |
| 3 | 0.27 | 6.0 | 9.6 |
| 4 | 0.37 | 7.8 | 9.1 |

| | DS | % COOH | % COOH (2) |
|---|---|---|---|
| 5 | 0 | 0 | 18.3 |
| 6 | 0.10 | 2.05 | 17.8 |
| 7 | 0.27 | 6.0 | 17.5 |
| 8 | 0.37 | 7.8 | 18.1 |

DS and % COOH-Designates carboxyl content due to carboxymethyl group
(1) % COOH-Designates carboxyl content due to 25 hour ring oxidation with dinitrogen tetroxide
(2) % COOH-Designates carboxyl content due to 55 hour ring oxidation with dinitrogen tetroxide

TABLE VI

| Base | Dicarboxyl form % COOH | Tricarboxyl form % COOH |
|---|---|---|
| Cellulose powder | 8.61 | 23.76 |
| Wood pulp fibers | 9.23 | 25.67 |
| Surgical gauze | 9.84 | 24.46 |
| Cellulose sponge | 8.55 | 24.95 |
| Amylose starch | 10.30 | 25.40 |

What is claimed is:

1. Absorbent, coherent, flexible cellulosic structures for application to the body comprising water-insoluble, ring oxidized cellulosic bases of the group of cellulose ethers, cellulose mixed ethers, cellulose ether mixed esters and mixtures thereof, the cellulosic bases having a DS of between about 0.05 and about 0.35, the ring oxidized forms of the cellulosic bases having a carboxyl content attributable to ring oxidation between about 2% and about 52%, said structures being further characterized in that when applied to the body and wet with aqueous body liquid the protruding fibrils and microfibrils on the surfaces and along the edges of the structures and the sharp edges of the structures become highly swollen almost instantaneously whereby the structures are non-irritating to the body over the area to which the structure is applied.

2. The structure according to claim 1 wherein the ring oxidized monocarboxyl forms of the cellulosic bases have a carboxyl content attributable to ring oxidation of about 2% to about 21%, the ring oxidized dicarboxyl forms of the cellulosic bases have a carboxyl content attributable to ring oxidation of about 7% to about 38% and the ring oxidized tricarboxyl forms of the cellulosic bases have a carboxyl content attributable to ring oxidation of about 12% to about 52%.

3. The structure according to claim 1 wherein the cellulosic base is derived from highly fibrillated wood pulp.

4. The structure according to claim 1 wherein the protruding fibrils and microfibrils upon becoming swollen dissolve in the body liquid.

5. The structure according to claim 1 further characterized by including a water-soluble dry binder whereby upon absorption of body liquid by the structure the dry binder dissolves and is leached from the structure.

6. The structure according to claim 1 further characterized by including as an impregnant ring oxidized starch.

7. The structure according to claim 1 further characterized by including as an impregnant succinylated gelatin.

8. The structure according to claim 1 in the form of a fibrous sheet.

9. The structure according to claim 1 in the form of a porous sponge.

10. The structure according to claim 1 being further characterized in absorbing at least about 1000% water.

11. The structure according to claim 1 wherein the cellulosic base is carboxymethyl cellulose.

12. The structure according to claim 1 wherein the cellulosic base is hydroxypropylmethyl cellulose.

13. The structure according to claim 1 wherein the cellulosic base is succinylated methyl cellulose or succinylated hydroxypropylmethyl cellulose and the structure being further characterized by exhibiting hemostatic properties.

14. The structure according to claim 1 in the form of a porous sponge and being further characterized by including an alkali soluble polyacrylate.

15. The structure according to claim 1 in the form of a porous sponge and being further characterized by including chitin derivatives of the group chitin ethers, chitin mixed ethers and chitin ether mixed esters and by exhibiting hemostatic properties.

16. The structure according to claim 1 in the form of a sponge wherein the cellulosic base is succinylated methyl cellulose or succinylated hydroxypropylmethyl cellulose and the structure being further characterized by including succinylated starch or succinylated hydroxypropylmethyl starch and by exhibiting hemostatic properties.

17. The structure according to claim 1 further characterized by including an aqueous isopropanol or aqueous ethanol soluble germicide, moldicide, bacteriocide or pharmaceutical agent.

18. The structure according to claim 1 further characterized by including another polymer.

* * * * *